(12) United States Patent
Chow Maneval et al.

(10) Patent No.: US 9,675,586 B2
(45) Date of Patent: *Jun. 13, 2017

(54) ESTROGEN RECEPTOR MODULATOR FOR THE TREATMENT OF LOCALLY ADVANCED OR METASTATIC ESTROGEN RECEPTOR POSITIVE BREAST CANCER

(71) Applicant: Genentech, Inc., South San Francisco, CA (US)

(72) Inventors: Edna Chow Maneval, San Diego, CA (US); Boa Tran H. Truong, San Diego, CA (US); Isan Chen, San Diego, CA (US); Jeffrey H. Hager, San Diego, CA (US); Debasish F. Roychowdhury, Lexington, MA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/561,701

(22) Filed: Dec. 5, 2014

(65) Prior Publication Data

US 2015/0157606 A1    Jun. 11, 2015

Related U.S. Application Data

(60) Provisional application No. 61/913,167, filed on Dec. 6, 2013, provisional application No. 61/981,672, filed on Apr. 18, 2014.

(51) Int. Cl.
*A61K 31/415* (2006.01)
*A61K 31/416* (2006.01)

(52) U.S. Cl.
CPC .................. *A61K 31/416* (2013.01)

(58) Field of Classification Search
USPC ....................................................... 514/406
See application file for complete search history.

(56) References Cited

U.S. PATENT DOCUMENTS

| 8,299,112 B2* | 10/2012 | Smith | .................. C07D 209/08 514/406 |
|---|---|---|---|
| 8,455,534 B2 | 6/2013 | Smith et al. | |
| 2012/0071535 A1 | 3/2012 | Smith et al. | |
| 2013/0231333 A1 | 9/2013 | Smith et al. | |
| 2015/0105403 A1 | 4/2015 | Smith et al. | |

FOREIGN PATENT DOCUMENTS

| WO | 2012/037410 A2 | 3/2012 |
|---|---|---|
| WO | 2012/037411 A2 | 3/2012 |
| WO | 2013/142266 A1 | 9/2013 |
| WO | 2014/151899 A1 | 9/2014 |

OTHER PUBLICATIONS

Groheux et al., "Estrogen Receptor-Positive/Human Epidermal Growth Factor Receptor 2-Negative Breast Tumors" Cancer 119(11):1960-68 ( 2013).
ISR for PCT/IB2014/002679, 2014.
Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts" Journal of Medicinal Chemistry 58(12):4888-4904 ( 2015).
Lips et al., "Neoadjuvant chemotherapy in on ER+ HER2− breast cancer:response prediction based on immunohistochemical and molecular characteristics" Breast Cancer Res Treat 131:827-36 (Apr. 2011).
Peterson et al., "Quantitative Imaging of Estrogen Receptor Expression in Breast Cancer with PET and 18F-Fluoroestradiol" Jour. of Nuclear Med. 49(3):367-74 ( 2008).
Choo, E.F. et al., "In vitro Drug-Drug Interaction Assessment of GDC-0810, a Novel and Potent Selective Estrogen Receptor Degrader" (Abstract #233) 28th EORTC-NCI-AACR Symposium, (2016).

* cited by examiner

*Primary Examiner* — Rei-Tsang Shiao
(74) *Attorney, Agent, or Firm* — Alex Andrus

(57) ABSTRACT

Described herein are methods of treating locally advanced or metastatic estrogen receptor positive breast cancer.

11 Claims, No Drawings

ESTROGEN RECEPTOR MODULATOR FOR THE TREATMENT OF LOCALLY ADVANCED OR METASTATIC ESTROGEN RECEPTOR POSITIVE BREAST CANCER

CROSS-REFERENCE

This application claims the benefit of U.S. Provisional Application No. 61/981,672, filed Apr. 18, 2014; and U.S. Provisional Application No. 61/913,167, filed Dec. 6, 2013, each of which is herein incorporated by reference in its entirety.

FIELD OF THE INVENTION

Described herein are methods of treating locally advanced or metastatic estrogen receptor positive breast cancer in women with the estrogen receptor modulator (E)-3-(4-((E)-2-(2-chloro-4-fluorophenyl)-1-(1H-indazol-5-yl)but-1-en-1-yl)phenyl)acrylic acid, or a pharmaceutically acceptable salt thereof.

BACKGROUND OF THE INVENTION

Breast cancer is the most common form of cancer and the leading cause of cancer death in women worldwide.

SUMMARY OF THE INVENTION

In one aspect, described herein is a method of treating locally advanced or metastatic estrogen receptor positive (ER+) breast cancer in a postmenopausal woman comprising administering a therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, to the postmenopausal woman in need thereof.

In some embodiments, the breast cancer is locally advanced or metastatic estrogen receptor positive, human epidermal growth factor receptor 2 negative (HER2−) breast cancer.

In some embodiments, the breast cancer in the postmenopausal woman had relapsed or progressed following no more than one prior therapy. In some embodiments, the breast cancer in the postmenopausal woman had relapsed or progressed following one or more prior therapies. In some embodiments, the breast cancer in the postmenopausal woman had relapsed or progressed following more than one prior therapy. In some embodiments, the prior therapy is an aromatase inhibitor. In some embodiments, the prior therapy is fulvestrant.

In some embodiments, the breast cancer in the postmenopausal woman had previously progressed in the presence of endocrine therapy. In some embodiments, the locally advanced breast cancer has progressed after greater than 6 months of endocrine therapy for ER+ breast cancer. In some embodiments, the metastatic breast cancer has progressed after greater than 6 months of endocrine therapy for ER+ breast cancer.

In some embodiments, the breast cancer in the postmenopausal woman had previously progressed in the presence of therapy with an aromatase inhbitor. In some embodiments, the aromatase inhibitor is aminoglutethimide, testolactone, anastrozole, letrozole, exemestane, vorozole, formestane, fadrozole, 4-hydroxyandrostenedione, 1,4,6-androstatrien-3,17-dione, or 4-androstene-3,6,17-trione. In some embodiments, the aromatase inhibitor is anastrozole, letrozole, or exemestane. In some embodiments, the aromatase inhibitor is anastrozole. In some embodiments, the aromatase inhibitor is letrozole. In some embodiments, the aromatase inhibitor is exemestane.

In some embodiments, the breast cancer is not amenable to resection or radiation therapy with curative intent.

In some embodiments, the breast cancer has progressed after at least 6 months of endocrine therapy for estrogen receptor positive breast cancer.

In some embodiments, the breast cancer in the postmenopausal woman had previously progressed in the presence of therapy with capecitabine, tamoxifen, everolimus, or fulvestrant. In some embodiments, the breast cancer in the postmenopausal woman had previously progressed in the presence of therapy with fulvestrant.

In another aspect, described herein is a method of treating hormone receptor positive metastatic breast cancer in a postmenopausal woman with disease progression following antiestrogen therapy comprising administering a therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, to the postmenopausal woman in need thereof. In some embodiments, the hormone receptor positive metastatic breast cancer is estrogen receptor positive metastatic breast cancer. In some embodiments, the estrogen receptor positive metastatic breast cancer is human epidermal growth factor receptor 2 negative (HER2−) breast cancer. In some embodiments, the breast cancer in the postmenopausal woman had relapsed or progressed following no more than one prior therapy. In some embodiments, the breast cancer in the postmenopausal woman had relapsed or progressed following one or more prior therapies. In some embodiments, the breast cancer in the postmenopausal woman had relapsed or progressed following more than one prior therapy. In some embodiments, the breast cancer in the postmenopausal woman had previously progressed in the presence of endocrine therapy. In some embodiments, the locally advanced breast cancer has progressed after greater than 6 months of endocrine therapy for ER+ breast cancer. In some embodiments, the metastatic breast cancer has progressed after greater than 6 months of endocrine therapy for ER+ breast cancer. In some embodiments, the breast cancer in the postmenopausal woman had previously progressed in the presence of therapy with an aromatase inhbitor. In some embodiments, the aromatase inhibitor is aminoglutethimide, testolactone, anastrozole, letrozole, exemestane, vorozole, formestane, fadrozole, 4-hydroxyandrostenedione, 1,4,6-androstatrien-3,17-dione, or 4-androstene-3,6,17-trione. In some embodiments, the aromatase inhibitor is anastrozole, letrozole, or exemestane. In some embodiments, the breast cancer is not amenable to resection or radiation therapy with curative intent. In some embodiments, the breast cancer has progressed after at least 6 months of endocrine therapy for estrogen receptor positive breast cancer. In some embodiments, the breast cancer in the postmenopausal woman had previously progressed in the presence of therapy with capecitabine, tamoxifen, everolimus, or fulvestrant. In some embodiments, the breast cancer in the postmenopausal woman had previously progressed in the presence of therapy with fulvestrant.

In another aspect, described herein is a method of treating locally advanced or metastatic estrogen receptor positive (ER+) breast cancer in a postmenopausal woman, comprising (a) determining ER status of breast cancer tumors of a postmenopausal woman having breast cancer to identify ER+ breast cancer tumors; and (b) administering a therapeutically effective amount of (E)-3-(4-((E)-2-(2-chloro-4-fluorophenyl)-1-(1H-indazol-5-yl) but-1-en-1-yl)phenyl) acrylic acid, or a pharmaceutically acceptable salt thereof, to the postmenopausal woman having ER+ breast cancer tumors. In some embodiments, the determining step comprises whole body imaging using a detectable tracer that selectively binds ER. In some embodiments, the detectable tracer is labeled 17β-estradiol. In some embodiments, the imaging is by positon-emitting tomography (PET) and the detectable tracer is 16α-$^{18}$F-fluoro-17β-estradiol (FES).

In some embodiments of the above aspects, the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered orally to the postmenopausal woman.

In some embodiments of the above aspects, the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered daily to the postmenopausal woman.

In some embodiments of the above aspects, the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered orally to the postmenopausal woman on a continuous daily dosing schedule.

In some embodiments of the above aspects, the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is about 50 mg per day to about 2000 mg per day.

In some embodiments of the above aspects, the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is about 100 mg per day to about 2000 mg per day.

In some embodiments of the above aspects, the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is about 100 mg per day, about 200 mg per day, about 300 mg per day, about 400 mg per day, about 500 mg per day, about 600 mg per day, about 700 mg per day, about 800 mg per day, about 900 mg per day, about 1000 mg per day, about about 1100 mg per day, about 1200 mg per day, about 1300 mg per day, about 1400 mg per day, about 1500 mg per day, about 1600 mg per day, about 1700 mg per day, about 1800 mg per day, about 1900 mg per day, or about 2000 mg per day.

In some embodiments of any of the above aspects, the therapeutically effective amount of (E)-3-(4-((E)-2-(2-chloro-4-fluorophenyl)-1-(1H-indazol-5-yl)but-1-en-1-yl) phenyl)acrylic acid, or a pharmaceutically acceptable salt thereof, is administered once a day to the postmenopausal woman.

In some embodiments of any of the above aspects, the therapeutically effective amount of (E)-3-(4-((E)-2-(2-chloro-4-fluorophenyl)-1-(1H-indazol-5-yl)but-1-en-1-yl) phenyl)acrylic acid, or a pharmaceutically acceptable salt thereof, is administered twice a day to the postmenopausal woman in evenly divided doses.

In some embodiments of any of the above aspects, the therapeutically effective amount of (E)-3-(4-((E)-2-(2-chloro-4-fluorophenyl)-1-(1H-indazol-5-yl)but-1-en-1-yl) phenyl)acrylic acid, or a pharmaceutically acceptable salt thereof, is administered three times a day to the postmenopausal woman in evenly divided doses.

In some embodiments of any of the above aspects, the therapeutically effective amount of (E)-3-(4-((E)-2-(2-chloro-4-fluorophenyl)-1-(1H-indazol-5-yl)but-1-en-1-yl) phenyl)acrylic acid, or a pharmaceutically acceptable salt thereof, is administered more than three times a day to the postmenopausal woman in evenly divided doses.

In any of the aforementioned aspects, the effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered (i) once a day; or (ii) multiple times over the span of one day. In some embodiments, the effective amount of (E)-3-(4-((E)-2-(2-chloro-4-fluorophenyl)-1-(1H-indazol-5-yl)but-1-en-1-yl) phenyl)acrylic acid, or a pharmaceutically acceptable salt thereof, is administered once a day, twice a day, three times a day or four times a day.

In any of the aforementioned aspects the effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered continuously or intermittently. In some embodiments, the effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered continuously. In some embodiments, the effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered daily.

In some embodiments of any of the aforementioned aspects, the (E)-3-(4-((E)-2-(2-chloro-4-fluorophenyl)-1-(1H-indazol-5-yl)but-1-en-1-yl)phenyl)acrylic acid is administered to the postmenopausal woman in a fed state.

Other objects, features and advantages of the methods, uses and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Breast cancer is the most common form of cancer and the leading cause of cancer death in women worldwide. Approximately 80% of all breast cancers express and are dependent on the estrogen receptor (ER) for tumor growth and progression. Modulation of estrogen activity and/or synthesis is the mainstay of therapeutic approach in postmenopausal women with ER-positive (ER+) breast cancer. However, despite the effectiveness of available hormonal therapies such as tamoxifen, aromatase inhibitors (e.g., anastrozole, letrozole and exemestane) and full ER antagonists/degraders (e.g., fulvestrant), many patients ultimately relapse or develop resistance to these agents and therefore require further treatment for optimal disease control. As such, there is a need for the development of new ER-targeting therapies with increased anti-tumor activity to further delay disease progression and/or overcome resistance to the currently available hormonal therapies and ultimately prolong survival in postmenopausal women with ER+ advanced breast cancer.

Despite becoming refractory to aromatase inhibitors or tamoxifen, growth and survival of resistant tumor cells remain dependent on ER signaling; therefore, patients with ER+ breast cancer can still respond to second/third line hormonal treatment after progression on prior hormonal therapy. In some embodiments, in the endocrine resistant state, ER can signal in a ligand-independent manner. In some embodiments, an agent with a dual mechanism of action such as ER antagonism plus degradation has the potential to target both ligand-dependent and independent ER signaling and, consequently, improve treatment outcomes in late stage ER+ breast cancer.

Breast Cancer Stages

The stages of breast cancer are based on a number of factors, such as the size of the tumor, if cancer is found in the lymph nodes, and how far the cancer has spread. The stages are numbered 0, I, II, III or IV, with Stage I being the least advanced stage and Stage IV being the most advanced. Stage 0 is considered non-invasive breast cancer. Stages I-II is considered early breast cancer. Stage III is considered locally advanced breast cancer. Stage IV is considered metastatic breast cancer. These descriptions are broad descriptions of breast cancer stages, and may not include all possibilities.

In some embodiments, Stages I, IIA, and IIB (and some cancers of stage IIIA) are considered early breast cancer. At these stages, the cancer has not spread beyond the breast or the axillary lymph nodes (those under the arm).

In some embodiments, locally advanced breast cancer includes Stages IIIA, IIIB and IIIC. In some embodiments, Stage IIIA breast cancer includes instances when the tumor size is not large but the cancer has spread to many axillary (under the arm) lymph nodes or lymph nodes near the breastbone. In some other embodiments, Stage IIIA breast cancer includes instances when the tumor is large but there is less lymph node spread. Stage IIIB describes breast cancer in which the tumor has spread to the chest wall or the skin of the breast and may or may not have spread to lymph nodes. Stage IIIC describes cancer that has spread to lymph nodes below or above the collarbone, to many axillary (under the arm) lymph nodes, or to lymph nodes near the breastbone. The tumor may be of any size.

Stage IV describes metastatic breast cancer, which is cancer that has spread from the breast to other parts of the body, such as the bones (bone metastases) or the liver, lungs, or brain (visceral metastases).

In some embodiments, the methods disclosed herein target treatment of patients having locally advanced or metastatic ER+ breast cancer. In some embodiments, the ER+ metastatic breast cancer is human epidermal growth factor receptor 2 negative (HER2−) breast cancer. In some embodiments, the breast cancer had relapsed or progressed following no more than one prior therapy. In some embodiments, the breast cancer had relapsed or progressed following one or more prior therapies. In some embodiments, the breast cancer had relapsed or progressed following more than one prior therapy. In some embodiments, the breast cancer had previously progressed in the presence of endocrine therapy. In some embodiments, the locally advanced breast cancer has progressed after greater than 6 months of endocrine therapy for ER+ breast cancer. In some embodiments, the metastatic breast cancer has progressed after greater than 6 months of endocrine therapy for ER+ breast cancer. In some embodiments, the breast cancer had previously progressed in the presence of therapy with an aromatase inhbitor. In some embodiments, the aromatase inhibitor is aminoglutethimide, testolactone, anastrozole, letrozole, exemestane, vorozole, formestane, fadrozole, 4-hydroxyandrostenedione, 1,4,6-androstatrien-3,17-dione, or 4-androstene-3,6,17-trione. In some embodiments, the aromatase inhibitor is anastrozole, letrozole, or exemestane. In some embodiments, the breast cancer is not amenable to resection or radiation therapy with curative intent. In some embodiments, the breast cancer in the postmenopausal woman had previously progressed in the presence of therapy with capecitabine, tamoxifen, everolimus, or fulvestrant. In some embodiments, the breast cancer in the postmenopausal woman had previously progressed in the presence of therapy with fulvestrant. In some embodiments, the (E)-3-(4-((E)-2-(2-chloro-4-fluorophenyl)-1-(1H-indazol-5-yl) but-1-en-1-yl)phenyl)acrylic acid is administered to the postmenopausal woman in a fed state.

(E)-3-(4-((E)-2-(2-chloro-4-fluorophenyl)-1-(1H-indazol-5-yl) but-1-en-1-yl)phenyl)acrylic acid is a small molecule non-steroidal ERα antagonist that competes with estrogens for binding to the estrogen receptor with low nanomolar potency. In contrast to first generation ER antagonists, such as tamoxifen, (E)-3-(4-((E)-2-(2-chloro-4-fluorophenyl)-1-(1H-indazol-5-yl) but-1-en-1-yl)phenyl) acrylic acid fully antagonizes the response of ER to estrogens and induces proteosomal degradation of ER-α in breast cancer cell lines. These bipartite activities result in full antagonism of ER-target gene transcription in breast cancer cell lines in vitro. The result is robust inhibition of ER signaling, and in turn, inhibition of breast tumor cell proliferation. Unlike fulvestrant, which is also an ER antagonist and degrader, (E)-3-(4-((E)-2-(2-chloro-4-fluorophenyl)-1-(1H-indazol-5-yl)but-1-en-1-yl)phenyl)acrylic acid has a nonsteroidal chemical backbone and displays good oral bioavailability.

In vivo, (E)-3-(4-((E)-2-(2-chloro-4-fluorophenyl)-1-(1H-indazol-5-yl) but-1-en-1-yl)phenyl)acrylic acid exhibited dose dependent anti-tumor activity in both tamoxifen-sensitive and tamoxifen-resistant xenograft models of ER+ breast cancer. In all models, the efficacious dose range was 10-100 mg/kg/day, and all doses were very well tolerated. Efficacy in tamoxifen-resistant xenograft models correlated with efficient antagonist activity on ER target genes and reduction of ER-α tumor levels. Despite displaying similar transcriptional and ER degrader activities, fulvestrant appeared to be less efficacious than (E)-3-(4-((E)-2-(2-chloro-4-fluorophenyl)-1-(1H-indazol-5-yl)but-1-en-1-yl) phenyl)acrylic acid in these models.

Disclosed herein is the use of (E)-3-(4-((E)-2-(2-chloro-4-fluorophenyl)-1-(1H-indazol-5-yl) but-1-en-1-yl)phenyl) acrylic acid, or a pharmaceutically acceptable salt thereof, in the treatment of locally advanced or metastatic estrogen receptor positive breast cancer in a postmenopausal woman. In some embodiments, the breast cancer is locally advanced or metastatic estrogen receptor positive, human epidermal growth factor receptor 2 negative (HER2−) breast cancer. In some embodiments, the breast cancer in the postmenopausal woman had previously progressed in the presence of hormonal therapy. In some embodiments, the breast cancer is not amenable to resection or radiation therapy with curative intent. In some embodiments, the breast cancer has progressed after at least 6 months of endocrine therapy for estrogen receptor positive breast cancer. In some embodiments, the breast cancer in the postmenopausal woman had previously progressed in the presence of therapy with fulvestrant.

In another aspect, described herein is the use of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, in the treatment of hormone receptor positive metastatic breast cancer in a postmenopausal woman with disease progression following antiestrogen therapy. In some embodiments, the hormone receptor positive metastatic breast cancer is estrogen receptor positive metastatic breast cancer. In some embodiments, the estrogen receptor positive metastatic breast cancer is human epidermal growth factor receptor 2 negative (HER2−) breast cancer.

(E)-3-(4-((E)-2-(2-Chloro-4-fluorophenyl)-1-(1H-indazol-5-yl)but-1-en-1-yl)phenyl)acrylic acid is described in US Patent Publication no. 2013/0231333.

Pharmaceutically acceptable salts of (E)-3-(4-((E)-2-(2-chloro-4-fluorophenyl)-1-(1H-indazol-5-yl)but-1-en-1-yl) phenyl)acrylic acid include, but are not limited to: (1) acid addition salts, formed by reacting the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when the acidic proton present in the compound is replaced by a metal ion, e.g., an alkali metal ion (e.g. lithium, sodium, potassium), an alkaline earth ion (e.g. magnesium, or calcium), or an aluminum ion. In some cases, the compound coordinates with an organic base, such as, but not limited to, ethanolamine, diethanolamine, triethanolamine, tromethamine, N-methylglucamine, dicyclohexylamine, tris(hydroxymethyl)methylamine. In other cases, the compound herein forms a salt with an amino acid such as, but not limited to, arginine, lysine, and the like. Acceptable inorganic bases used to form a salt with the compound, include, but are not limited to, aluminum hydroxide, calcium hydroxide, potassium hydroxide, sodium carbonate, sodium hydroxide, and the like.

CERTAIN TERMINOLOGY

The term "cancer" as used herein refers to an abnormal growth of cells which tend to proliferate in an uncontrolled way and, in some cases, to metastasize (spread).

The term "breast cancer" as used herein refers to histologically or cytologically confirmed adenocarcinoma of the breast.

The term "locally advanced breast cancer" refers to cancer that has spread from where it started in the breast to nearby tissue or lymph nodes, but not to other parts of the body.

The term "metastatic breast cancer" refers to cancer that has spread from the breast to other parts of the body, such as the bones, liver, lungs, or brain. Metastatic breast cancer is also referred to as stage IV breast cancer.

The terms "effective amount" or "therapeutically effective amount," as used herein, refer to a sufficient amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, being administered which will relieve to some extent one or more of the symptoms of the disease or condition being treated. The result can be reduction and/or alleviation of the signs, symptoms, or causes of a disease, or any other desired alteration of a biological system.

The term "continuous daily dosing schedule" refers to the administration of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, daily without any drug holidays. In some embodiments, a continuous daily dosing schedule comprises administration of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, everyday at roughly the same time each day.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, delaying progression of condition, relieving a condition caused by the disease or condition, or stopping the symptoms of the disease or condition either prophylactically and/or therapeutically. In some embodiments, treatment includes extending progression-free survival. In some embodiments, treatment includes extending disease-free survival. In some embodiments, treatment includes reducing the relative risk of disease progression compared to other treatment options. In some embodiments, other treatment options include but are not limited to hormonal treatments (e.g. antiestrogen therapy, such as tomoxifen and/or fulvestrant).

The term "progression-free survival" is the amount of time during and after the treatment of a disease, such as cancer, that a patient lives with the disease but it does not get worse. In a clinical trial, measuring progression-free survival is one way to see how well a treatment works.

The term "disease-free survival" (DFS) refers to the length of time after treatment for a cancer ends that the patient survives without any signs or symptoms of that cancer In a clinical trial, measuring disease-free survival is one way to see how well a treatment works. In some embodiments, the increase in the DFS is about 1 month, about 2 months, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months.

The term "metastasis-free survival" or "MFS" refers to the percentage of subjects in a study who have survived without cancer spread for a defined period of time or death. MFS is usually reported as time from the beginning of treatment in the study. MFS is reported for an individual or a study population. In some embodiments, the increase in the metastasis-free survival is about 1 month, about 2 months, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months.

Routes of Administration

Suitable routes of administration of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, include, but are not limited to, oral administration. In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered in the form of a dispersion, solution, suspension, tablet, capsule, or pill. All formulations for oral administration are in dosages suitable for such administration. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, can vary widely depending on the severity of the disease, the age and relative health of the subject, and other factors.

The term "acceptable" with respect to a formulation, composition or ingredient, as used herein, means having no persistent detrimental effect on the general health of the female human being treated.

Methods of Dosing and Treatment Regimens

In some embodiments, (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered orally to postmenopausal women.

In some embodiments, (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered daily to postmenopausal women. In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered every other day to postmenopausal women. In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered daily, every other day, every third day, every fourth day, every fifth day, every sixth day, once a week, once every two weeks, once every three weeks, or once a month to postmenopausal women.

In some embodiments, (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered orally to postmenopausal women on a continuous daily dosing schedule.

In some embodiments, about 50 mg per day to about 4000 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 50 mg per day to about 3000 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 50 mg per day to about 2000 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 50 mg per day to about 1000 mg per day of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered to postmenopausal women.

In some embodiments, about 100 mg per day to about 2000 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women.

In some embodiments, about 50 mg per day, about 100 mg per day, about 150 mg per day, about 200 mg per day, about 250 mg per day, about 300 mg per day, about 350 mg per day, about 400 mg per day, about 450 mg per day, about 500 mg per day, about 550 mg per day, about 600 mg per day, about 650 mg per day, about 700 mg per day, about 750 mg per day, about 800 mg per day, 850 mg per day, about 900 mg per day, about 950 mg per day, about 1000 mg per day, about 1050 mg per day, about 1100 mg per day, about 1150 mg per day, about 1200 mg per day, about 1250 mg per day, about 1300 mg per day, about 1350 mg per day, about 1400 mg per day, about 1450 mg per day, about 1500 mg per day, about 1550 mg per day, about 1600 mg per day, about 1650 mg per day, about 1700 mg per day, about 1750 mg per day, about 1800 mg per day, about 1850 mg per day, about 1900 mg per day, about 1950 mg per day, about 2000 mg per day, about 2050 mg per day, about 2100 mg per day, about 2150 mg per day, about 2200 mg per day, about 2250 mg per day, about 2300 mg per day, about 2350 mg per day, about 2400 mg per day, about 2450 mg per day, about 2500 mg per day, about 2550 mg per day, about 2600 mg per day, about 2650 mg per day, about 2700 mg per day, about 2750 mg per day, about 2800 mg per day, about 2850 mg per day, about 2900 mg per day, about 2950 mg per day, or about 3000 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women.

In some embodiments, about 100 mg per day, about 200 mg per day, about 300 mg per day, about 400 mg per day, about 500 mg per day, about 600 mg per day, about 700 mg per day, about 800 mg per day, about 900 mg per day, about 1000 mg per day, about 1100 mg per day, about 1200 mg per day, about 1300 mg per day, about 1400 mg per day, about 1500 mg per day, about 1600 mg per day, about 1700 mg per day, about 1800 mg per day, about 1900 mg per day, or about 2000 mg per day of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered to postmenopausal women.

In some embodiments, about 100 mg per day, about 200 mg per day, about 400 mg per day, about 600 mg per day, about 800 mg per day, about 1000 mg per day, about 1200 mg per day, about 1400 mg per day or about 1600 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women.

In some embodiments, about 100 mg per day of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered to postmenopausal women. In some embodiments, about 200 mg per day of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered to postmenopausal women. In some embodiments, about 400 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, bout 600 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 800 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 1000 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 1200 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 1400 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women. In some embodiments, about 1600 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to postmenopausal women.

In one embodiment, the desired daily dose is conveniently presented in a single dose or in divided doses administered simultaneously (or over a short period of time) or at appropriate intervals, for example as two, three, four or more sub-doses per day. In some embodiments, the desired daily dose is conveniently presented in divided doses that are administered simultaneously (or over a short period of time) once a day. In some embodiments, the desired daily dose is conveniently presented in divided doses that are administered in equal portions twice-a-day, three times a day, or more than three times a day.

In some embodiments, the desired daily amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, that is administered to postmenopausal women is administered once a day.

In some embodiments, the daily amount of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, that is administered to postmenopausal women is administered twice a day in evenly divided doses.

In some embodiments, the daily amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, that is administered to postmenopausal women is administered three times a day in evenly divided doses.

In some embodiments, the daily amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, that is administered to postmenopausal women is administered more than three times a day in evenly divided doses.

In certain embodiments wherein improvement in the status of the breast cancer in the postmenopausal woman is not observed, the daily dose of (E)-3-(4-((E)-2-(2-chloro-4-fluorophenyl)-1-(1H-indazol-5-yl)but-1-en-1-yl)phenyl) acrylic acid, or a pharmaceutically acceptable salt thereof, is increased. In some embodiments, a once-a-day dosing schedule is changed to a twice-a-day dosing schedule. In some embodiments, a three times a day dosing schedule is employed to increase the amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, that is administered.

In some embodiments, (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is administered to the postmenopausal woman in the fasted state. In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered to the postmenopausal woman in the fed state.

In some embodiments, the amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, that is given to postmenopausal women varies depending upon factors such as, but not limited to, condition and severity of the breast cancer, and the identity (e.g., weight) of the woman.

As described in the Examples, imaging with [18F]-fluoroestradiol (FES) positron emitting tomography (PET) is performed to quantify ER expression in the tumor and to assess for pharmacodynamic response to therapy with (E)-3-(4-((E)-2-(2-chloro-4-fluorophenyl)-1-(1H-indazol-5-yl) but-1-en-1-yl)phenyl)acrylic acid, or a pharmaceutically acceptable salt thereof. In some embodiments, PET images are taken pre-dosing with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, and then following continuous dosing. In some embodiments, PET images are taken on day 29 following continuous dosing. In some embodiments, PET images are taken between day 2 and day 60 following continuous dosing. In some embodiments, PET images are taken between day 2 and day 30 following continuous dosing. In some embodiments, PET images are taken between day 2 and day 15 following continuous dosing. In some embodiments, PET images are taken between day 16 and day 30 following continuous dosing. In some embodiments, PET images are taken at about 2-24 hours post dose. In some embodiments, PET images are taken at about 2-20 hours post dose, about 2-12 hours post dose, about 2-10 hours post dose, about 18-24 hours post dose or about 20-24 hours post dose. In some embodiments, PET images are taken at about 2 hours post dose, about 6 hours post dose, about 8 hours post dose, about 10 hours post dose, about 12 hours post dose, about 14 hours post dose, about 16 hours post dose, about 18 hours post dose, about 20 hours post dose, or about 24 hours post dose. In some embodiments, PET images are taken at about 10 hours post dose for patients receiving 100 mg/day, 200 mg/day or 400 mg/day. In some embodiments, PET images are taken at about 20 hours post dose for patients receiving 600 mg/day or 800 mg/day or 1000 mg/day or 1200 mg/day or 1400 mg/day or 1600 mg/day.

In some embodiments, full target occupancy is observed at ≥200 mg/day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof.

In some embodiments, (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, is observed to displace greater than 50%, greater than 55%, greater than 60%, greater than 65%, greater than 70%, greater than 75%, greater than 80%, greater than 85%, greater than 90%, or greater than 95% of [18F]-fluoroestradiol (FES) from target tumor tissues.

In some embodiments, administration of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, provides a greater than 50%, greater than 55%, greater than 60%, greater than 65%, greater than 70%, greater than 75%, greater than 80%, greater than 85%, greater than 90%, or greater than 95% reduction in the maximum standardized uptake value (SUV).

As described in the Examples, tumor biopsies (soft tissue or visceral lesions) are collected pre- and post-treatment with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof. In some embodiments, the tumor biopsies provide information regarding the effect of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, on ER target genes expression. Examples of ER target genes thay maybe monitored include, but are not limited to: AGR2, AREG, C3, CCND1, CXCL12, ERBB2, GREB1, IL6, IRS1, PDZK1, PGR, SEMA3B, TFF1, TFF2, TFF3, TOP2A, WISP2. In some embodiments, ER cytoplasmic protein levels are reduced >25%, >30%, >35%, >40%, >45%, >50%, >55%, >60%, >65%, >70%, >75%, >80%, >85%, >90%, >95%, >96% or >98% in ER+ breast cancer cells as judged by immunohistochemistry of tumor samples from patients treated with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, as compared to a pre-treatment biopsy. In some embodiments, ER nuclear protein levels are reduced >25%, >30%, >35%, >40%, >45%, >50%, >55%, >60%, >65%, >70%, >75%, >80%, >85%, >90%, >95%, >96% or >98% in ER+ breast cancer cells as judged by immunohistochemistry of tumor biopsies from patients treated with (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, as compared to a pre-treatment biopsy. In some embodiments, proliferative index as judged by Ki67 marker is reduced >25%, >30%, >35%, >40%, >45%, >50%, >55%, >60%, >65%, >70%, >75%, >80%, >85%, >90%, >95%, >96% or >98% in ER+ breast cancer cells as judged by immunohistochemistry of tumor biopsies from patients treated with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, as compared to a pre-treatment biopsy. In some embodiments, patients were treated with 100 mg/day, 200 mg/day, 400 mg/day, 600 mg/day, 800 mg/day, 1000 mg/day, 1200 mg/day, 1400 mg/day or 1600 mg/day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof.

In some embodiments, whole body imaging with 16α-$^{18}$F-fluoro-17β-estradiol or [18F]-fluoroestradiol (FES or $^{18}$F-FES) positron emitting tomography (PET) is performed on postmenopausal women having breast cancer to assess ER expression in breast cancer tumors, wherein women with ER+ breast cancer tumors are selected for therapy with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof. Whole body imaging for ER expression using may be performed using methods known in the art (see, e.g., Krutchen et al. Journal of Nuclear Medicine 53(2):182-190, 2012).

In some embodiments, described herein is a method of treating locally advanced or metastatic estrogen receptor positive (ER+) breast cancer in a postmenopausal woman, comprising (a) determining ER status of breast cancer tumors of a postmenopausal woman having breast cancer using $^{18}$F-FES-PET to identify ER+ breast cancer tumors; and (b) administering a therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, to the postmenopausal woman having ER+ breast cancer tumors.

EXAMPLES

These examples are provided for illustrative purposes only and not to limit the scope of the claims provided herein.

Example 1: Clinical Trial of (E)-3-(4-((E)-2-(2-chloro-4-fluorophenyl)-1-(1H-indazol-5-yl) but-1-en-1-yl)phenyl)acrylic acid in Postmenopausal Women with Locally Advanced or Metastatic ER+ Breast Cancer This is an open label clinical trial evaluating the efficacy and safety of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, in post-menopausal women with locally advanced or metastatic ER+ (HER2−) breast cancer.
Primary Objective:
To determine the Maximum Tolerated Dose (MTD) and/or Recommended Phase 2 Dose (RP2D) and assess the safety of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, in post-menopausal women with locally advanced or metastatic ER+ (HER2−) breast cancer
Secondary Objectives:
To evaluate the pharmacokinetics (PK) of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, following single and multiple dose treatments (e.g. $C_{max}$, $T_{max}$, AUC, $T_{1/2}$). If the safety and PK profile seen in the Phase I (dose escalation) portion of the study are deemed favorable to justify further continuation of the study, dose escalation will be followed by an expansion cohort to further confirm safety and tolerability and assess preliminary evidence of antitumor activity (Phase IIa). Additional objectives include: perform exploratory evaluation of biomarkers of pharmacodynamic (PD) response with [$^{18}$F]-fluoroestradiol (FES) positron emitting tomography (PET) [FES PET]; perform exploratory evaluation of ER target genes expression; perform exploratory evaluation of mechanisms of resistance to (E)-3-(4-((E)-2-(2-chloro-4-fluorophenyl)-1-(1H-indazol-5-yl) but-1-en-1-yl)phenyl)acrylic acid, or a pharmaceutically acceptable salt thereof.
Trial Design:
Women in the Phase I portion of the study will be assigned to escalating doses of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, in cohorts of 3-6 patients per dose until determination of the maximum tolerated dose (MTD) and/or recommended Phase 2 Dose (RP2D) using standard 3+3 criteria. A starting dose of 100 mg per day of (E)-3-(4-((E)-2-(2-chloro-4-fluorophenyl)-1-(1H-indazol-5-yl)but-1-en-1-yl)phenyl) acrylic acid, or a pharmaceutically acceptable salt thereof, will be administered, followed by dose escalation to 200 mg, and by 200 mg increments thereafter. During Phase IIa (dose expansion), a new cohort of patients will be enrolled at the MTD/RP2D to further characterize the safety and pharmacokinetics of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof.

The MTD and/or RP2D will be defined as the dose with ≤1 out of 6 patients with Dose Limiting Toxicity (DLT). Dose Limiting Toxicity (DLT) Definition: Any Grade ≥3 non-hematology toxicity (excluding alopecia); Any Grade ≥3 hematology toxicity >7 days; Any Grade toxicity that leads to study drug interruption >7 days.

Phase IIa:

An expansion cohort consisting of a total of approximately 70 postmenopausal women with locally advanced or metastatic ER+ (HER2−) breast cancer will be treated at the MTD/RP2D to further characterize the safety, PK, and anti-tumor activity of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof as follows:

Expansion Cohort:

70 patients who have progressed following no more than 1 prior therapy with an aromatase inhibitor in the advanced/metastatic setting.

All patients will be treated until disease progression, unacceptable toxicity, or patient withdrawal of consent.

Patient Selection

Phase I—Inclusion Criteria

1. Histologically or cytologically proven diagnosis of adenocarcinoma of the breast with evidence of either locally recurrent disease not amenable to resection or radiation therapy with curative intent, or metastatic disease, both progressing after at least 6 months of endocrine therapy for ER+ breast cancer.

2. ER-positive tumor (staining in ≥1% cells by immunohistochemistry [IHC] as per local laboratory testing).

3. HER2-negative breast cancer as per local laboratory testing (IHC result of 0 or +1 for cellular membrane protein expression or a FISH result showing HER2/CEP17 ratio<1.8 or an average of fewer than 4 copies of HER2 gene per nucleus for systems without an internal control probe).

4. At least 2 months must have elapsed from the use of tamoxifen.

5. At least 6 months must have elapsed from the use of fulvestrant.

6. At least 2 weeks must have elapsed from the use of any other anti-cancer hormonal therapy.

7. At least 3 weeks must have elapsed from the use of any chemotherapy

8. Females, 18 years of age or older.

9. Postmenopausal status defined as:

Prior bilateral surgical oophorectomy

Age≥56 years: natural amenorrhea with ≥1 year since last menses

Age<56 years with amenorrhea ≥1 year since last menses and serum estradiol levels (<20 pg/mL) and FSH levels (>40 mIU/mL) in the postmenopausal range Age<56 years who had hysterectomy with one or both ovaries left in place, or with tamoxifen-induced amenorrhea together with a tamoxifen discontinuation of ≥1 year and serum estradiol levels (<20 pg/mL) and FSH levels (>40 mIU/mL) in the postmenopausal range Age<56 years who have medical menopause on LHRH agonist (on stable dose ≥1 year) with amenorrhea ≥1 year together with a tamoxifen discontinuation of ≥1 year and serum estradiol levels (<20 pg/mL) in the postmenopausal range irrespective of FSH/LH levels 10. Eastern Cooperative Oncology Group (ECOG) Performance status≤2.

11. Resolution of all acute toxic effects of prior therapy or surgical procedures to baseline or Grade ≤1 (except alopecia or other toxicities not considered to be a safety risk for the patient).

12. Adequate organ function as defined by the following criteria:

Absolute neutrophil count (ANC)≥1500/μL

Platelets≥100,000/μL

Serum aspartate transaminase (AST) and serum alanine transaminase (ALT)≤3×upper limit of normal (ULN), or AST and ALT≤5×ULN if liver function abnormalities are due to underlying malignancy Total serum bilirubin≤1.5×ULN regardless of liver involvement secondary to tumor. Inclusion of patients with increased serum indirect bilirubin (≤3×ULN) due to Gilbert's syndrome is permitted Serum creatinine≤1.5×ULN 13. Signed and dated informed consent document indicating that the subject (or legally acceptable representative) has been informed of all the pertinent aspects of the trial prior to enrollment 14. Willingness and ability to comply with scheduled visits, treatment plan, laboratory tests, and other trial procedures Phase I—Exclusion Criteria 1. Untreated or symptomatic CNS metastases. Note: Patients with treated and asymptomatic CNS metastases that are radiographically stable within 12 weeks prior to enrollment will be allowed, provided long-term use of corticosteroids have been discontinued within 4 weeks prior to enrollment 2. Endometrial disorders 3. More than 2 prior chemotherapies in the advanced/metastatic setting (prior adjuvant chemotherapy is allowed so long as it occurred ≥12 months prior to enrollment)

4. Current treatment with any systemic anti-cancer therapies for advanced disease or any systemic experimental treatment on another clinical trial 5. Diagnosis of any secondary malignancy within 2 years prior to enrollment, except for adequately treated basal cell or squamous cell skin cancer, or carcinoma in situ 6. Any of the following within 12 months prior to enrollment: myocardial infarction, severe/unstable angina, ongoing cardiac dysrhythmias of Grade ≥2, atrial fibrillation of any grade, coronary/peripheral artery bypass graft, symptomatic congestive heart failure, or cerebrovascular accident including transient ischemic attack 7. Active inflammatory bowel disease or chronic diarrhea, short bowel syndrome, or upper gastrointestinal surgery including gastric resection 8. Known human immunodeficiency virus infection 9. Major surgery or radiation therapy within 4 weeks prior to enrollment 10. Other severe acute or chronic medical or psychiatric condition or laboratory abnormality that may increase the risk associated with study participation or investigational product administration or may interfere with the interpretation of study results and, in the judgment of the Investigator, would make the subject inappropriate for entry into this study Phase IIa—Inclusion Criteria 1. Histologically or cytologically proven diagnosis of adenocarcinoma of the breast with evidence of either locally recurrent disease not amenable to resection or radiation therapy with curative intent, or metastatic disease, both progressing after at least 6 months of endocrine therapy for ER+ breast cancer.

2. ER-positive tumor (staining in ≤1% cells by immunohistochemistry [IHC] as per local laboratory testing).

3. HER2-negative breast cancer as per local laboratory testing (IHC result of 0 or +1 for cellular membrane protein expression or a FISH result showing HER2/CEP17 ratio<1.8 or an average of fewer than 4 copies of HER2 gene per nucleus for systems without an internal control probe).

4. Disease progression following no more than 1 prior treatment with an AI in the advanced/metastatic setting (prior adjuvant treatment with an aromatase inhibitor is allowed):

Patients must have relapsed ≥12 months from completion of adjuvant treatment or progressed following ≥6 months of treatment in the advanced/metastatic setting Cohort 1 only: no prior fulvestrant allowed Cohort 2 only: prior fulvestrant allowed.

5. At least 2 weeks must have elapsed from the use of the most recent endocrine therapy.

6. At least 3 weeks must have elapsed from the use of any chemotherapy

7. Females, 18 years of age or older

8. Postmenopausal status defined as:

Prior bilateral surgical oophorectomy

Age≥56 years: natural amenorrhea with ≥1 year since last menses

Age<56 years with amenorrhea ≥1 year since last menses and serum estradiol levels (<20 pg/mL) and FSH levels (>40 mIU/mL) in the postmenopausal range Age<56 years who had hysterectomy with one or both ovaries left in place, or with tamoxifen-induced amenorrhea together with a tamoxifen discontinuation of ≥1 year and serum estradiol levels (<20 pg/mL) and FSH levels (>40 mIU/mL) in the postmenopausal range Age<56 years who have medical menopause on LHRH agonist (on stable dose ≥1 year) with amenorrhea ≥1 year since last menses and serum estradiol levels (<20 pg/mL) in the postmenopausal range irrespective of FSH/LH levels.

9. Eastern Cooperative Oncology Group (ECOG) Performance status 0 or 1.

10. Resolution of all acute toxic effects of prior therapy or surgical procedures to baseline or Grade ≤1 (except alopecia or other toxicities not considered to be a safety risk for the patient).

11. Adequate organ function as defined by the following criteria:

Absolute neutrophil count (ANC)≥1500/μL

Platelets≥100,000/μL

Serum aspartate transaminase (AST) and serum alanine transaminase (ALT)≤3×upper limit of normal (ULN), or AST and ALT≤5×ULN if liver function abnormalities are due to underlying malignancy Total serum bilirubin≤1.5×ULN regardless of liver involvement secondary to tumor. Inclusion of patients with increased serum indirect bilirubin (≤3×ULN) due to Gilbert's syndrome is permitted Serum creatinine≤1.5×ULN QTc≤460 msec 12. Signed and dated informed consent document indicating that the subject (or legally acceptable representative) has been informed of all the pertinent aspects of the trial prior to enrollment 13. Willingness and ability to comply with scheduled visits, treatment plan, laboratory tests, and other trial procedures Phase IIa—Exclusion Criteria 1. Untreated or symptomatic CNS metastases. Note: Patients with treated and asymptomatic CNS metastases that are radiographically stable within 12 weeks prior to enrollment will be allowed, provided long-term use of corticosteroids have been discontinued within 4 weeks prior to enrollment.

2. Endometrial disorders.

3. Prior treatments:

| Exclusions | Prior Edocrine Therapy | Prior Chemotherapy |
|---|---|---|
| Cohort 1 | >1 prior aromatase inhibitor in the advanced setting<br>Fulvestrant | Prior chemotherapy in the advanced/metastatic setting (prior adjuvant chemotherapy is allowed so long as it occurred ≥12 months prior to enrollment) |
| Cohort 2 | >1 prior aromatase inhibitor in the advanced setting | >1 prior chemotherapy in the advanced/metastatic setting |

4. Current treatment with any systemic anti-cancer therapies for advanced disease or any systemic experimental treatment on another clinical trial.

5. Prior treatment with any investigational agent.

6. Diagnosis of any secondary malignancy within 2 years prior to enrollment, except for adequately treated basal cell or squamous cell skin cancer, or carcinoma in situ.

7. Any of the following within 12 months prior to enrollment: myocardial infarction, severe/unstable angina, ongoing cardiac dysrhythmias of Grade ≥2, atrial fibrillation of any grade, coronary/peripheral artery bypass graft, symptomatic congestive heart failure, or cerebrovascular accident including transient ischemic attack.

8. Active inflammatory bowel disease or chronic diarrhea, short bowel syndrome, or upper gastrointestinal surgery including gastric resection.

9. Known human immunodeficiency virus infection.

10. Major surgery within 4 weeks prior to enrollment.

11. Radiation therapy within 2 weeks prior to enrollment.

12. Other severe acute or chronic medical or psychiatric condition or laboratory abnormality that may increase the risk associated with study participation or investigational product administration or may interfere with the interpretation of study results and, in the judgment of the Investigator, would make the subject inappropriate for entry into this study.

Tumor Assessments

Disease assessments will be performed. Imaging studies will include a CT scan of the chest, abdomen, and pelvis, plus a bone scan. Radiographic confirmation of objective tumor response or disease progression will be based on RECIST v1.1 (Eisenhauer, 2009). For new bone lesions detected on bone scans, a second imaging modality (e.g., CT or MRI) will be required to confirm progression.

The same method of assessment and the same technique should be used at Screening and during follow up. Intravenous (IV) contrast is required when not medically contraindicated. Patients who have a contraindication to IV contrast may have MRI exams of the abdomen and pelvis performed in lieu of CTs and a non-contrast CT of the chest. Tumor evaluation by positron emission tomography (PET) scan or by ultrasound may not substitute for CT.

Correlative Studies
Pharmacodynamics with [18]FES-PET Target Engagement

Imaging with [18F]-fluoroestradiol (FES) positron emitting tomography (PET) will be performed to quantify ER expression in the tumor and to assess for pharmacodynamic response to therapy with (E)-3-(4-((E)-2-(2-chloro-4-fluorophenyl)-1-(1H-indazol-5-yl) but-1-en-1-yl)phenyl)acrylic acid, or a pharmaceutically acceptable salt thereof. While FES uptake can vary between patients, in general, the FES uptake is fairly consistent across lesions at a given time point, and the average uptake provides a reasonable summary of ER expression for an individual patient. Factors that can affect the standardized uptake value (SUV), such as sex hormone-binding globulin (SHBG), will be adjusted as needed (Peterson, 2011). In addition, a washout period for patients previously treated with tamoxifen (at least 2 months) or fulvestrant (at least 6 months) may be required due to the long half-life of each drug and their potential to interfere with FES uptake. FES-PET studies will be performed as hybrid PET/CT imaging for attenuation correction and lesion localization.

Core Biopsies

Pre- and post-treatment tumor biopsies (soft tissue or visceral lesions) will be collected to evaluate:

Tumor Histology; tumor vs. stroma, vs fibrotic tissue

ERα and PR protein levels by immunohistochemistry or immunofluorescence

Proliferative Index (Ki67)

ER target gene modulation: Examples of ER target genes thay maybe monitored include, but are not limited to: AGR2, AREG, C3, CCND1, CXCL12, ERBB2, GREB1, IL6, IRS1, PDZK1, PGR, SEMA3B, TFF1, TFF2, TFF3, TOP2A, WISP2.

Circulating Tumor DNA (ctDNA)

In all patients during Phase I (dose escalation) and Phase IIa (dose expansion), additional blood samples will be collected at Screening, Cycle 3 Day 1, Cycle 6 Day 1, and at the time of study discontinuation for analysis of circulating tumor DNA (ctDNA).

Example 2: Phase I Clinical Trial of (E)-3-(4-((E)-2-(2-chloro-4-fluorophenyl)-1-(1H-indazol-5-yl)but-1-en-1-yl)phenyl)acrylic acid in Postmenopausal Women with Locally Advanced or Metastatic ER+ Breast Cancer A preliminary analysis of the first 41 patients enrolled in the Phase I study described in Example 1 was conducted. 41 patients were enrolled in the Phase I portion of the study, across 9 different dose escalation cohorts. The patients were postmenopausal women with advanced or metastatic breast cancer that had previously relapsed or progressed following prior therapy with the aromatase inhibitors anastrozole, exemestane, and letrozole (90%), chemotherapy (68%), including capecitabine (27%), tamoxifen (54%), fulvestrant (41%), everolimus (19%), and also other investigational agents (17%).

(E)-3-(4-((E)-2-(2-chloro-4-fluorophenyl)-1-(1H-indazol-5-yl) but-1-en-1-yl)phenyl)acrylic acid was safe and well tolerated in 41 patients with advanced or metastatic breast cancer who had progressed on a median of 4 prior treatments. The pharmacokinetic profile was linear and dose proportional, with target plasma concentrations achieved at or above 600 mg QD. There was robust target engagement across multiple dose levels via FES-PET imaging and evidence of reduced ER and Ki-67 levels in tumor specimens. The preliminary overall clinical benefit rate was 42%; 35% in patients previously treated with fulvestrant.

The examples and embodiments described herein are for illustrative purposes only and various modifications or changes suggested to persons skilled in the art are to be included within the spirit and purview of this application and scope of the appended claims.

What is claimed is:

1. A method of treating hormone receptor positive metastatic breast cancer in a postmenopausal woman with disease progression following antiestrogen therapy comprising administering a therapeutically effective amount of (E)-3-(4-((E)-2-(2-chloro-4-fluorophenyl)-1-(1H-indazol-5-yl) but-1-en-1-yl)phenyl)acrylic acid, or a pharmaceutically acceptable salt thereof, to the postmenopausal woman in need thereof, wherein the hormone receptor positive metastatic breast cancer is estrogen receptor positive metastatic breast cancer, and wherein the postmenopausal woman had been previously treated with antiestrogen therapy comprising treatment with capecitabine, tamoxifen, fulvestrant, or everolimus.

2. The method of claim 1, wherein the estrogen receptor positive metastatic breast cancer is human epidermal growth factor receptor 2 negative (HER2−) breast cancer.

3. The method of claim 1, wherein the breast cancer in the postmenopausal woman had previously progressed in the presence of therapy with an aromatase inhibitor.

4. The method of claim 1, wherein the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered orally to the postmenopausal woman.

5. The method of claim 1, wherein the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered daily to the postmenopausal woman.

6. The method of claim 1, wherein the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is administered orally to the postmenopausal woman on a continuous daily dosing schedule.

7. The method of claim 1, wherein the therapeutically effective amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is about 50 mg per day to about 2000 mg per day.

8. The method of claim 1, wherein the (E)-3-(4-((E)-2-(2-chloro-4-fluorophenyl)-1-(1H-indazol-5-yl)but-1-en-1-yl)phenyl)acrylic acid is administered to the postmenopausal woman in a fed state.

9. The method of claim 1, wherein antiestrogen therapy comprises treatment with tamoxifen.

10. The method of claim 1, wherein antiestrogen therapy comprises treatment with fulvestrant.

11. The method of claim 3, wherein the aromatase inhibitor is anastrozole, letrozole, or exemestane.

* * * * *